US00PP11683P

United States Patent [19]

van Andel

[11] Patent Number: Plant 11,683

[45] Date of Patent: Dec. 12, 2000

[54] ALSTROEMERIA PLANT NAMED 'STAPRILENE'

[75] Inventor: Jacob van Andel, Aalsmeer, Netherlands

[73] Assignee: Van Staaveren B.V., Aalsmeer, Netherlands

[21] Appl. No.: 09/226,316

[22] Filed: Jan. 6, 1999

[51] Int. Cl.[7] ..... A01H 5/00

[52] U.S. Cl. ..... Plt./309

[58] Field of Search ..... Plt./309

*Primary Examiner*—Howard J. Locker

*Attorney, Agent, or Firm*—Christie, Parker & Hale, LLP

[57] ABSTRACT

A new and distinct Alstroemeria plant variety producing flowers of good quality and attractive coloration.

1 Drawing Sheet

BACKGROUND OF THE INVENTION

The present invention relates to a new and distinct variety of Alstromeria which is a cross of two unnamed, undistributed seedlings; namely, 80D421 as seed parent and 90F1412 as pollen parent. The varietal denomination of the new variety is 'Staprilene'.

The first act of asexual reproduction of 'Staprilene' was in Aalsmeer, The Netherlands, by propagation by dividing the rhizomes. Asexual reproduction by dividing rhizomes through successive generations in Aalsmeer, The Netherlands, has demonstrated that the combination of characteristics as herein disclosed for 'Staprilene' are firmly fixed and retained through successive generations.

SUMMARY OF THE INVENTION

The new variety of Alstroemeria, 'Staprilene', produces large flowers.

DESCRIPTION OF ILLUSTRATION

The new variety of Alstroemeria hybrid is illustrated in the accompanying illustration, which shows typical flower characteristics, with colors being as nearly true as is possible for illustrations of this type.

DETAILED DESCRIPTION OF THE NEW VARIETY

The following is a detailed description of the new cultivar of Alstroemeria hybrid as observed in a greenhouse in Aalsmeer, The Netherlands. Color designations indicated are in accordance with The Royal Horticultural Society Colour Chart by color plate designations.

'Staprilene' has not been observed under all possible environmental conditions. Phenotypic expression may vary with variations in environment such as temperature, light intensity, day length and growing and cultural conditions.

Botanical classification:

*Family*.—Amaryllidaceae.

*Genus*.—Alstroemeria sp.

Plant:

*Form*.—Bush.

*Shape*.—Upright.

*Main stem*.—About 20 to 45 cm.

*Internode length*.—About 0.5 to 2 cm.

*Growth*.—Vigorous.

*Strength*.—Strong.

*Blooming habit*.—Continuous.

Foliage:

*Number of leaves*.—About 10 to 20 per stem.

*Size of leaf*.—Length: About 2 to 10 cm. Width: About 1 to 3 cm.

*Shape of leaf*.—Elliptic.

*Margin*.—Straight, entire.

*Texture*.—Glossy.

*Color*.—Upper side: Near 137A. Underside: Near 137C.

Flower:

*Blooming habit*.—Continuous, profusely throughout the year.

*Size* (*when first anthers release pollen*).—Diameter: About 6 cm. Depth: About 5 cm.

*Borne*.—About 3 to 6 blooms per umbel.

*Shape or form*.—When bloom first opens: Cup. When bloom matures: Cup.

*Fragrance*.—None.

*Lasting quality*.—On plant: About 4 weeks, As cut flower: About 18–20 days.

*Rhizomes*.—Plant about 1 to 2 year old. Color: Near 155D. Size: About 10 to 30 cm.

*Tepalage*.—Number of tepals: About 6. Arrangement: 2 concentric circles of 3 tepals. Shape: Inner tepals, long obovate; outer tepals, obovate. Margin: Minutely crimped. Apex: Pointed.

*Color*.—Outer tepals: Upper surface — Base near 4D, body near 4D with area of near 143A at center extreme-distal portion of tepal, about 0–5 spots, spots near 185A in coloration; Under surface — body near 4D, with central area of near 143A extending along substantially the length of the tepal to distal end. Inner lateral tepals: Upper surface — Base near 4D, body near 4D with central area of near 6A, about 20–40 spots, spots near 185A in coloration; Under surface — Base near 4D, body near 4D with central area of near 6A. Inner median tepal: Upper surface — Base near 4D, body near 4D, about 3–10 spots, spots near 185A in coloration; Under surface coloration is similar to that of upper surface.

*Peduncle length*.—About 1 to 5 cm. Color: Near 137B. Strength: Strong, erect. Discoloration: No discoloration after full bloom, not hairy.

*Persistence*.—Flower does not hang on and dry.

*Disease resistance*.—Unknown.

Bud:

*Size*.—Diameter: About 1 to 2 cm. Depth or length: About 2 to 4 cm.

*Form*.—Pear-shaped.

*Rate of opening*.—Fast.

*Color of tepals when tepals first divide*.—Near 4D and 143 A.

*Color of tepals when tepals begin to unfurl*.—Near 4D and 143A.

Reproductive organs:

*Stamen*.—Number: About 6. Arrangement: Side by side around the style.

*Anthers*.—Size: About 8 to 10 mm. Color Near 164B.

*Filaments*.—Length: 5 cm. Color: Near 36 B.

*Pollen*.—Color: Near 166 C.

*Pistils*.—1. Styles: Length about 4 to 5 cm. Color: Near 36 B.

*Stigmas*.—Color: Near 36B.

Fruit: Fertile.

*Shape*.—Round.

*Color at maturity*.—Near 163A.

I claim:

1. A new and distinct Alstroemeria plant of the variety substantially as shown and described.

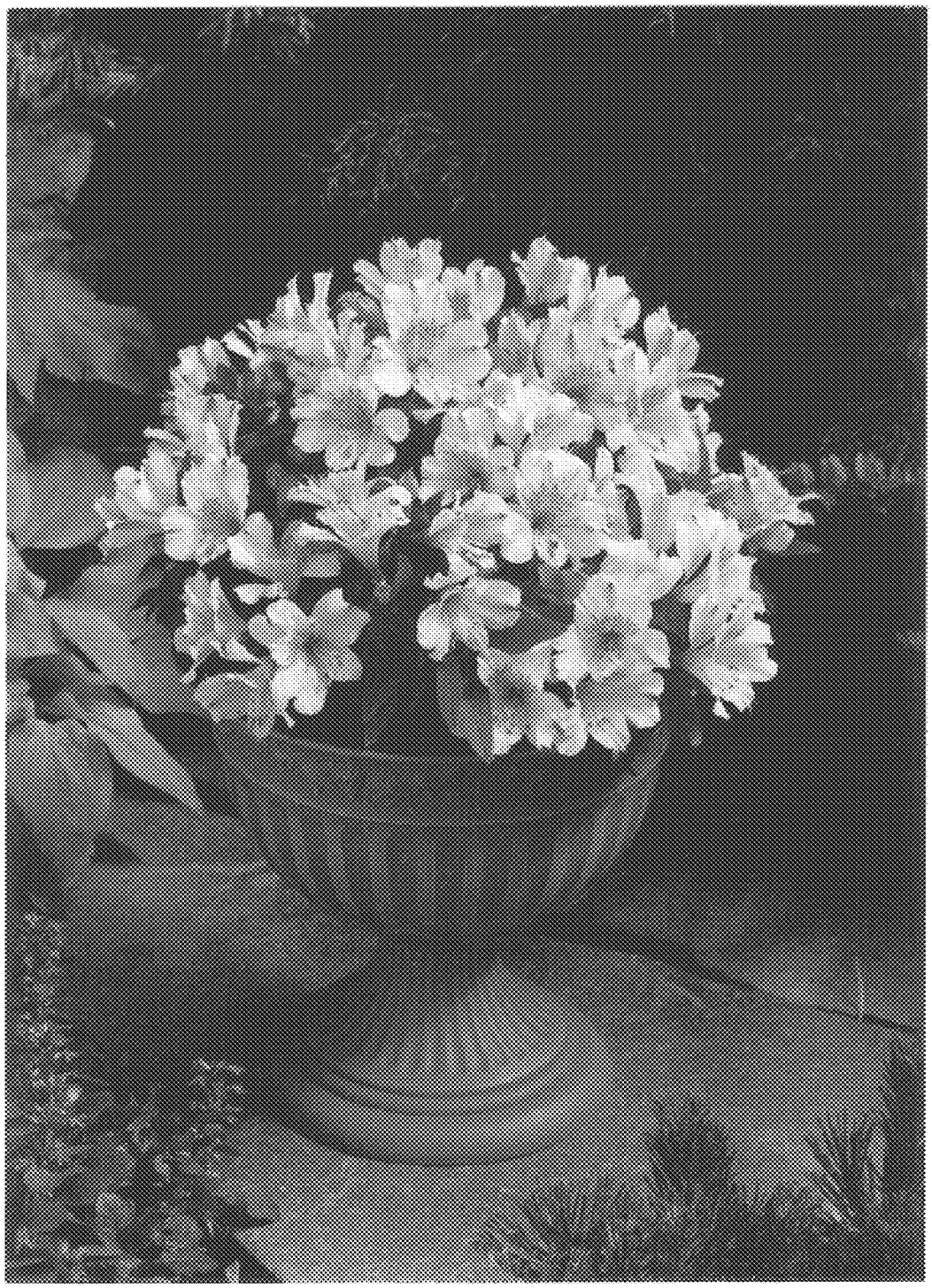

* * * * *